(12) United States Patent
Javois et al.

(10) Patent No.: US 10,813,649 B2
(45) Date of Patent: Oct. 27, 2020

(54) DEVICE FOR CLOSING AN ATRIAL APPENDAGE

(71) Applicant: PFM MEDICAL AG, Cologne (DE)

(72) Inventors: Alex Javois, Hinsdale, IL (US); Thilo Wack, Nonnweiler (DE); Franz Freudenthal, La Paz (BO)

(73) Assignee: PFM MEDICAL AG, Cologne (DE)

( * ) Notice: Subject to any disclaimer, the term of this patent is extended or adjusted under 35 U.S.C. 154(b) by 292 days.

(21) Appl. No.: 15/080,981

(22) Filed: Mar. 25, 2016

(65) Prior Publication Data

US 2016/0278749 A1 Sep. 29, 2016

Related U.S. Application Data

(60) Provisional application No. 62/139,088, filed on Mar. 27, 2015.

(30) Foreign Application Priority Data

Mar. 27, 2015 (DE) .................. 10 2015 104 785

(51) Int. Cl.
*A61B 17/12* (2006.01)

(52) U.S. Cl.
CPC .. *A61B 17/12145* (2013.01); *A61B 17/12122* (2013.01); *A61B 17/12172* (2013.01)

(58) Field of Classification Search
CPC ........ A61B 17/12109; A61B 17/12113; A61B 17/12118; A61B 17/12122; A61B 17/1214; A61B 17/12145; A61B 17/1215; A61B 17/12168; A61B 17/12172; A61B 17/12177; A61B 2017/00575;
(Continued)

(56) References Cited

U.S. PATENT DOCUMENTS 6,290,674 B1 9/2001 Roue et al.
6,652,556 B1 11/2003 Vantassel et al.
(Continued)

FOREIGN PATENT DOCUMENTS

DE 102009036818 2/2011
DE 102010021345 11/2011
(Continued)

*Primary Examiner* — Katherine H Schwiker
(74) *Attorney, Agent, or Firm* — Grossman, Tucker, Perreault & Pfleger, PLLC

(57) ABSTRACT

The invention relates to a device for closing an atrial appendage, particularly the left atrial appendage, comprising a closing element, designed to be arranged in an atrial appendage entrance and to prevent an entrance of blood into the atrial appendage and/or a leakage of thrombus out of the atrial appendage, which is configured that it does not, in the implanted state, protrude out of the atrial appendage into the atrium of the heart; a first anchoring element, which is arranged adjacent to the closing element and connected to the closing element, wherein the first anchoring element is designed for an anchoring on an atrial appendage tissue wall, a connecting element which is at least in a radial direction flexible and connected to the first anchoring element and a second anchoring element, which is connected to the connecting element and designed for an anchoring on an atrial appendage tissue wall.

29 Claims, 8 Drawing Sheets

(58) Field of Classification Search
CPC ........... A61B 2017/00592; A61B 2017/00597; A61B 2017/00632; A61B 17/0057; A61B 17/12022; A61B 2017/00601
USPC ........................................................ 606/200
See application file for complete search history.

(56) References Cited

U.S. PATENT DOCUMENTS

| | | | |
|---|---|---|---|
| 2002/0111647 A1* | 8/2002 | Khairkhahan | A61B 17/0057 606/200 |
| 2004/0098031 A1 | 5/2004 | Van Der Burg et al. | |
| 2004/0215230 A1 | 10/2004 | Frazier et al. | |
| 2005/0038470 A1* | 2/2005 | van der Burg | A61B 17/0057 606/213 |
| 2005/0113861 A1 | 5/2005 | Corcoran et al. | |
| 2007/0270891 A1 | 11/2007 | McGuckin, Jr. | |
| 2008/0033241 A1 | 2/2008 | Peh et al. | |
| 2009/0099647 A1* | 4/2009 | Glimsdale | A61B 17/12113 623/1.35 |
| 2009/0112249 A1* | 4/2009 | Miles | A61B 17/12122 606/192 |
| 2011/0196413 A1* | 8/2011 | Wallace | A61B 17/12022 606/194 |
| 2012/0271337 A1* | 10/2012 | Figulla | A61B 17/0057 606/191 |
| 2012/0316584 A1* | 12/2012 | Miles | A61B 17/0057 606/157 |
| 2012/0323267 A1* | 12/2012 | Ren | A61B 17/12172 606/191 |
| 2014/0005714 A1* | 1/2014 | Quick | A61L 31/022 606/200 |

FOREIGN PATENT DOCUMENTS

| | | | |
|---|---|---|---|
| DE | 102012003021 | 10/2012 | |
| WO | 2007/140797 | 12/2007 | |
| WO | WO-2007140797 A1 * | 12/2007 | ....... A61B 17/12022 |
| WO | 2008/125689 | 10/2008 | |
| WO | 2008/147678 | 12/2008 | |
| WO | 2008/150346 | 12/2008 | |
| WO | 2012/003317 | 1/2012 | |

* cited by examiner

DEVICE FOR CLOSING AN ATRIAL APPENDAGE

CROSS-REFERENCE TO RELATED APPLICATIONS

This non-provisional application claims the benefit of U.S. Provisional Application No. 62/139,088 filed Mar. 27, 2015 as well as German Application No. 10 2015 104 785.3 filed Mar. 27, 2015. Both of which are incorporated herein.

FIELD

The invention relates to a device for closing an atrial appendage, in particular of the left atrial appendage.

BACKGROUND

The human heart is a hollow, muscular organ that pumps with rhythmic contractions blood through the body, thereby ensuring the supply of all organs. The human heart is functioning as a displacement pump, wherein using valves blood is sucked out of blood vessels and ejected into other blood vessels. The human heart has two smaller, upper chambers, which are called atria, and two larger, more powerful pumping chambers, which are called ventricles. The blood flows through the right atrium into the heart and subsequently fills the right ventricle. By contraction of the heart the blood is pumped through the pulmonary artery into the lungs, where it is filtered and oxygenated. The filtered and the oxygenated blood is pumped into the left atrium, and afterwards fills the left ventricle. From the left ventricle the blood is pumped through the aorta in the body to supply oxygen to all the organs and cells. After the blood has passed through the systemic circulation, it is low in oxygen and returns to the heart.

The atrial appendages (auriculae atrii) are protrusions of the atria of the heart. The right atrial appendage (auricula atrii dextra) is adjacent to the ascending aorta and the left atrial appendage (auricula atrii sinistra) is located next to the trunk of the pulmonary artery (truncus pulmonalis). The left atrial appendage is a common origin for thrombus, which can lead to a stroke, especially in case of patients with atrial fibrillation. The right atrial appendage is an origin of thrombus, which can lead to a pulmonary embolism. However, the emergence of pulmonary embolism caused by thrombus emerging from the right atrium is low compared to pulmonary embolism from other causes.

The left atrial appendage (LAA) is a muscular bag that is connected to the left atrium of the heart. The left atrial appendage is a normal part of the anatomy of the heart and goes back to the embryonic development of the heart. However, the left atrial appendage is a main source for the formation of thrombus in case of patients with atrial fibrillation. Such thrombus can for example block blood flow to the brain and cause a stroke, which can lead to temporary or permanent brain or organ damage.

Atrial fibrillation is caused by irregular electrical impulses in the upper chambers of the heart which trigger a vibration or tremor. This leads to an irregular and often rapid heartbeat and can cause a reduced blood flow, heart palpitations and shortness of breath. Moreover, during atrial fibrillation thrombus can form in the left atrial appendage. After the heart rhythm normalizes, these thrombus can emerge from the left atrial appendage into the left atrium and from there into the oxygen-rich blood flow.

To prevent strokes in case of atrial fibrillation, in modern medicine a device is used for the closure of the atrial appendages an alternative or in addition to a drug treatment or surgical removal of the left atrial appendage. A prevention of stroke by means of drugs, for example with vitamin-k-antagonist, leads to an increased rate of intracerebral hemorrhage. Surgical removal of the left atrial appendage is a serious surgical procedure and thus subject to an increased risk.

The aforesaid disadvantages are avoided by a device for closing the left atrial appendage. All techniques of interventional atrial appendage closure base on a venous transeptal access, via which a self-expanding device is introduced using a fluoroscopic visualization of the left atrial appendage. Advantageously a device for closing the left atrial appendage can be implanted using a minimally invasive procedure.

A device for closing an atrial appendage must be selected such that it completely closes the atrial appendage regardless of the anatomy of the atrial appendage and must not replace its location after a successful implantation. This depends in particular on the anatomy of the atrial appendage. The anatomy of atrial appendages is basically divided into three types. In type 1 (Collar) the atrial appendage entrance is smaller than the largest diameter within the atrial appendage. In a type 2 (funnel-shaped) atrial appendage, the diameter of the atrial appendage entrance is larger than the largest diameter within the atrial appendage and a type 3 (tubular) atrial appendage has an atrial appendage entrance that has approximately the same size as the atrial appendage behind the entrance. All other types of atrial appendages, like e. g. cauliflower or chicken wing type atrial appendages, can be subsumed under one of the above mentioned three basic types.

DE 10 2009 036 818 A1 discloses a LAA occlusion device consisting of a highly elastic metal material with memory properties. The LAA occlusion device is provided with a circular cover at the proximal end and has a spherical coupling with a through hole in the proximal retention area. The distal retention area of the LAA occlusion device has the form of a lip. Behind the maximum diameter of the LAA occlusion device a strong tapering is arranged next to a very flexible bar, wherein the taper is movable so that the distal retention area of the LAA occlusion device can be angled relative to the circular cover up to 900. To anchor the LAA occlusion device barbs are provided at the distal edge of the proximal retention area. However, using barbs involves in principle a risk to perforate the tissue wall of the atrial appendage, which may lead to internal bleeding. If the circular cover on the proximal end does not fully contact the tissue of the heart, the period within which the LAA occlusion device is overgrown with endothelial tissue increases.

DE 10 2010 021 345 A1 relates to an occlusion device for closing an atrial appendage with a self-expandable occluder made of a metal tube by laser cutting. The occluder receives its shape by means of a molding and heat treatment process. The occluder has a front facing proximal retention area and a rear facing distal retention area, wherein at the proximal end region the laser cut rod-shaped elements converge in a fastener. In the collapsed state the occluder can be introduced minimally invasive in a patient's body by means of a catheter and placed in the atrial appendage. The occluder includes a section with knobs between the proximal retention area and the center region, for forming a friction-locked connection between the knob section of the occluder and the atrial appendage wall. The use of knobs reduces the risk of a perforation of the atrial appendage wall compared to the use of barbs. However, the occlusion device uses a disc-shaped proximal retention area, which is overgrown significantly slower by endothelial tissue in case it does not completely contact the wall of the heart, like the aforementioned occlusion device according to DE 10 2009 036 818 A1.

From DE 10 2012 003 021 A1 an occlusion device for closing an atrial appendage is known, comprising a first section at a proximal end of the occlusion device, which is adapted to the diameter of an atrial appendage entrance and a second portion that is adapted to the length of the atrial appendage, wherein the closure of the atrial appendage is accomplished by two superimposed membranes located in the second portion at the distal end of the occlusion device which are adapted to correct the length of the occlusion device. For anchoring of the occlusion device barb elements are provided. The closure of the atrial appendage the occlusion device has a disc-shaped portion at the proximal end. Furthermore, DE 10 2012 003 021 A1 discloses with respect to a tubular atrial appendage, that the atrial appendage occlusion device does not need a disc-shaped proximal portion, in case that the shape of the occlusion device corresponds exactly to the shape of the atrial appendage entrance. A disadvantage of the occlusion device is that it is fixed by means of barb elements in the atrial appendage. When using a disk-shaped proximal portion the aforementioned problems with respect to an overgrowth with endothelial tissue arise. Regarding the embodiment without a disc-shaped proximal portion it is disadvantageous that the proximal portion must match exactly the shape of the atrial appendage entrance.

WO 2012/003317 A1 discloses a device for closing an atrial appendage comprising an occluder disc configured to substantially prevent blood flow to or from the atrial appendage; a central region with a spiral element, said spiral element is connected to the occluder disc, has a substantially constant cross-section and is adjustable at least in the length, orientation and angle to the occluder disc; and a first anchor member which is connected to the spiral member and which has an uneven edge which is formed such that the occlusion device can be anchored on the inner wall of the atrial appendage without the risk of penetration or perforation of the atrial appendage wall. A disadvantage of the occlusion device is the use of an occluder disc which is overgrown by endothelial tissue after a long time period in case of a non-exact positioning relative to the heart wall.

WO 2007/140797 A1 discloses an occlusion device for closing an atrial appendage with a self-expanding occlusion body consisting of a mesh of thin wires or threads, the braid is given a suitable shape by means of a molding and heat treatment process, wherein the occlusion body has a rear-facing distal retention area and a front-facing proximal retention area, wherein at the proximal retention area the ends of the wires or threads of the mesh converge into a holder, and wherein the occlusion body further comprises a central region between the distal and proximal retention areas, wherein the occlusion body in the folded state can be introduced minimally invasive into the body of a patient and positioned in the atrial appendage by means of a catheter. The occlusion device further comprises fixing means with a polymer network which is formed by means of a polyreaction mechanism, preferably taking place in the patient's atrial appendage, and which establishes a force-fit connection between the braid of the occlusion body and the wall of the atrial appendage. After the positioning of the occlusion body it is necessary that the fixing means is inserted, particular as a low viscosity liquid, which is applied and controllable cured to a flexible non-solvable product using a cannulae, into the atrial appendage to fix the occlusion device in the atrial appendage. It is thus necessary to insert a low viscous fixing agent into the occlusion device positioned in the atrial appendage without applying any of the fixing agent outside the atrial appendage.

WO 2008/125689 A1 discloses an occlusion device and a manufacturing method thereof. The occlusion device consists of a network of at least one wire or thread, wherein the occlusion device receives its desired shape using a shaping and/or heat treatment process, is expandable and configured for secure anchoring in an atrial appendage of the left or right atrium of the heart. The occlusion member comprises a proximal retention area in the form of a disc at a proximal end of the occlusion device; a distal retention area; and a middle portion between the proximal retention area and the distal retention area; said occlusion device having a closed distal end without a socket and wherein the occlusion device is at least partially formed spherical and hollow. A disadvantage of such an occlusion device is the use of the disk-shaped proximal retention area, which is in case of a non-exact positioning slowly overgrown by endothelial tissue.

U.S. Pat. No. 6,290,674 B1 discloses a device for closing an atrial appendage. The device consists of rods which are fixed by means of hooks in the wall of the atrial appendage. The use of hooks to fix the device, however, can lead to internal bleeding.

US 2004/215230 A1 discloses an occlusion device for an atrial appendage, which is fixed by means of an element engaging the tissue of the atrial appendage. As stated with respect to the aforementioned occlusion devices a penetration of the tissue of the atrial appendage by a fixing element has the risk of internal bleeding.

WO 2008/150346 A1 discloses a filter device which prevents the leakage of thrombus from an atrial appendage. The device is fixed with hooks inside the atrial appendage, which has the aforementioned disadvantages.

US 2007/270891 A1 discloses a device for closing an atrial appendage. The device is formed spirally and surrounded by a membrane. The device is fixed inside of the atrial appendage by means of retaining elements, which engage into the tissue of the atrial appendage.

Known from US 2004/0098031 A1 is a device for closing an atrial appendage also comprises fixing means which engage into the tissue of the atrial appendage. Furthermore, the disclosed device uses a disk-shaped closing element.

US 2008/0033241 A1 discloses a device for closing an atrial appendage, which is fixed by a retaining element in the atrial appendage, wherein the retaining element is anchored in the tissue wall of the atrial appendage. Furthermore, a clamp is disclosed to close the entrance of an atrial appendage, wherein the clamp engages the vessel wall of the atrial appendage.

US 2005/0113861 A1 discloses a device for closing an atrial appendage. The device comprising a support member and ribs extending from the proximal end to the distal end of the post, wherein the ribs are curved in such a way that the device rests against the inner wall of the atrial appendage and is thus fixed. A membrane is stretched around and/or between the ribs, which prevents a blood flow into the atrial appendage. In order to securely fix the device in the atrial appendage, the device must be exactly adapted to the size and anatomy of the atrial appendage.

The device known from WO 2008/147678 A1 is used to grab an atrial appendage from the outside and to block the inner atrial appendage from the atrium of the heart using a loop.

U.S. Pat. No. 6,652,556 B1 discloses a filter device for an atrial appendage. The filter device is placed in such a way in front of the atrial appendage opening that blood can pass through the filter device, while thrombus cannot pass through the filter device from the interior of the atrial appendage into the atrium of the heart.

SUMMARY

It is therefore an object of the present invention to avoid the disadvantages known from the prior art, particularly to provide a device for closing an atrial appendage which can be anchored independently of the anatomy of the atrial appendage safely in the atrial appendage without damaging the tissue of the atrial appendage, and which is as soon as possible overgrown by endothelial tissue.

According to the invention the object is solved by a device for closing an atrial appendage, particularly the left atrial appendage, comprising a closing element, designed to be arranged in an atrial appendage entrance and to prevent an entrance of blood into the atrial appendage and/or a leakage of thrombus out of the atrial appendage, which is configured that it does not, in the implanted state, protrude out of the atrial appendage into the atrium of the heart; a first anchoring element, which is arranged adjacent to the closing element and connected to the closing element, wherein the first anchoring element is designed for an anchoring on an atrial appendage tissue wall; a connecting element, which is at least in a radial direction flexible and connected to the first anchoring element; and a second anchoring element, which is connected to the connecting element and designed for an anchoring on an atrial appendage tissue wall.

The use of a closing element arranged in an atrial appendage entrance has the advantage compared to the use of a disc shaped retention area, which is arranged in the atrium of the heart next to the atrial appendage entrance, that the closing element contacts the wall of the atrial appendage entrance with the whole circumference. Thereby it is ensured, that the closing element is overgrown by endothelial tissue as quickly as possible. In contrast to this the use of a disc shaped retention area does not guarantee that the disc shaped retention area contacts the wall of the heart and overgrow with endothelial tissue only occurs when the endothelial tissue grows to this area from other areas where the disc shaped retention area is in contact with the wall of the heart and already overgrown by endothelial tissue. Furthermore the closing element according to the invention guarantees that no thrombus can enter the atrium of the heart from the atrial appendage by passing between the closing element and the wall of the heart.

The first anchoring element, which is arranged adjacent to the closing element and connected to the closing element, guarantees that the closing element is secured within the atrial appendage entrance and that the closing element cannot relocate from the atrial appendage entrance into the atrium of the heart.

The second anchoring element is used to enhance the anchoring of the device in the atrial appendage. The second anchoring element is connected to the first anchoring element via the connecting element. The connecting element is in a radial direction flexible since the anatomy of atrial appendages differs in particularly because an atrial appendage usually does not perpendicularly stick out of the wall of the heart but lies against the wall of the heart and is therefore angled to the atrial appendage entrance.

The first anchoring element and the second anchoring element are designed for an anchoring on an atrial appendage tissue wall. An anchoring on an atrial appendage tissue wall in the sense of the invention excludes an anchoring in the atrial appendage tissue wall as well as a perforation of the atrial appendage tissue wall.

According to a variant of the invention the diameter of the closing element is larger than the atrial appendage entrance. Advantageously the diameter of the closing element is between 5% and 20% larger than the atrial appendage entrance, particularly about 10%. Since the diameter of the closing element is larger than the atrial appendage entrance it is guaranteed that the closing element contacts the wall of atrial appendage entrance with the whole circumference. Furthermore thereby an additional anchoring and centering of the closing element in the atrial appendage entrance is achieved.

According to a variant of the invention the closing element comprises a first membrane element, wherein the first membrane element is impermeable to thrombus. For example the first membrane element is porous and does not prevent a blood flow between the atrial appendage and the atrium but does prevent a transition of thrombus from the atrial appendage into the atrium of the heart. Furthermore a porous first membrane element supports an overgrow of the first membrane element with endothelial tissue because of the small porous size. Alternatively the first membrane element can be impermeable for fluids.

According to an alternative or additional variant of the invention the closing element comprises a second membrane element, wherein the second membrane element is designed to support an overgrow of the closing element with endothelial tissue. An overgrow of the closing element with endothelial tissue ensures that the closing element is securely fixed within the atrial appendage entrance and furthermore the impermeability of the closing element with respect to the blood flow out of the atrial appendage is guaranteed over an unspecified period.

Advantageously the first membrane element and the second membrane element are built integrally. By integrally building the first membrane element and the second membrane element only one element has to be connected to the closing element, for example by gluing, welding, sewing, fusing, dipmoulding or any other method of joining. Advantageously the first membrane element and/or the second membrane element or the integral membrane element is permanently connected to the closing element.

Preferably the closing element and the first membrane element and/or the second membrane element or the integral membrane element are detachable or inseparable connected or connectable to each other, particularly by gluing, welding, sewing, fusing, dip-coating or another joining technology.

According to a further variant of the invention the first membrane element and/or the second membrane element or the integral membrane element can comprise a coating to establish a biostability and/or biocompatibility. Biostability in the sense of the invention refers to the biological, chemical and/or physical stress at the implantation side. Biocompatibility in the sense of the invention refers to the integration of the device in the biological environment at the implantation side, preferably without irritating, for example by the material quality, shape and function, the surrounding tissue.

For example the first membrane element and/or the second membrane element and/or the integral membrane element comprise at least one of the following materials: polyester, polytetrafluorethylene (PTFE), expended/extruded PTFE, teflon, felt, goretex, siliconeurethane, metal fibers and polypropylene. In general, the first membrane element and/or the second membrane element or the integral membrane element can consist of a synthetical or biological material, particularly of a bioresorbable material.

According to a particularly preferred variant of the invention the first membrane element and/or the second membrane element or the integral membrane element completely covers the atrial appendage entrance in the implanted state of the device. Thereby the impermeability of the atrial appendage entrance with respect to a transfer of thrombus out of the atrial appendage is ensured as well as an overgrow of the atrial appendage entrance with endothelial tissue.

According to a further variant of the invention the first membrane element and/or the second membrane element or the integral membrane element enclose the rim of the closing element in such a way, that the first membrane element and/or the second membrane element or the integral membrane element completely contact the atrial appendage tissue wall in the implanted state of the device. The direct contact between the membrane element and the atrial appendage tissue wall enhances the impermeability of the atrial appendage entrance and further supports an overgrow of the membrane element and therefore of the closing element with endothelial tissue. For example the first membrane element and/or the second membrane element or the integral membrane element enclose the rim of the closing element and extend into the direction of the first anchoring member, e. g. half way down to the first anchoring member.

In an inventive variant the closing element is cylindrical, conical, tapered and/or truncated cone-shaped. Thus, the closing element extends over a defined region in the longitudinal direction of the device, for example the closing element extends over a length of 0.5 cm to 2.5 cm in the longitudinal direction of the device. This has the advantage that the contact area between the closing element and the atrial appendage entrance is enlarged, whereby the anchoring of the closing element is enhanced and further the impermeability is guaranteed and an overgrow of the closing element with endothelial tissue is supported.

According to an advantageously variant of the invention the surface of the closing element directed towards the atrium of the heart is smooth. Thus, no parts of the inventive device extend into the atrium of the heart.

In a preferred variant of the invention the closing element and the first anchoring element are securely fixed to one another or build integrally.

The connecting element is preferably connected to the first anchoring element via a first connection and/or connected to the second anchoring element via a second connection. Advantageously the first connection and the second connection are located on opposing ends of the connecting element. Generally the first anchoring element is located at one end of the connecting element and the second anchoring element is located on an opposing end of the connecting element. The first connection and/or the second connection are preferably built in such a way that they cannot be separated after the implantation.

According to an advantageous variant of the invention the connecting element is cylindrical. A cylindrical connecting element particularly provides the flexibility in a radial direction. Furthermore such a cylindrical connecting element can be easily made by cutting, particularly laser cutting a tube.

For example the connecting element is helical.

According to a variant of the invention the connecting element is made of a tube, particularly by cutting apertures into the tube, for example using a laser. For instance from a tube a helical connecting element can be cut which is cylindrical and flexible in a radial direction.

In a particularly preferred variant of the invention the closing element, the first anchoring element and/or the second anchoring element is formed from a single wire-type element or multiple wire-type elements by intercoiling and/or interwining and/or interweaving like a tissue and/or a cluster and/or a net. This guarantees a good stability in the implanted state and at the same time the device is flexible during the implantation so that the device can be implanted via a minimal invasive method. For example the closing element and the first anchoring element are made of a single wire-type element or multiple wire-type elements and the second anchoring element is made of a further single wire-type element or further multiple wire-type elements. Alternatively the closing element, the first anchoring element and the second anchoring element can be made of a single wire-type element or multiple wire-type elements. A single wire-type element can also consist of several elements for example like a litz wire or several single wires extending parallel to each other. In case of multiple wire-type elements these elements are preferably clustered at a single point of the device, e. g. in a mounting. The wire-type elements have for example a round or oval cross section.

Furthermore the device can comprise several layers of the tissue and/or a cluster and/or a net.

In a further preferred variant of the invention the closing element, the first anchoring element and the second anchoring element consist of a shape memory material, particularly of nitinol or a plastic with memory shape effect. The use of shape memory material facilitates the minimal invasive implantation of the inventive device.

In a further inventive variant the device comprises a radio-opaque marking, particularly a marker, marking tag or marking wire. Thus, during the implantation of the inventive device the positioning of the device can be monitored using an imaging method like e. g. x-ray or magnetic resonance imaging.

According to a further variant of the invention the first anchoring element and/or the second anchoring element is disc-shaped or umbrella-shaped and particularly extends in a radial direction. Particularly the first anchoring element and/or the second anchoring element is bulbous and/or curved. Such embodiments are particularly suitable for anchoring the device at the atrial appendage tissue wall.

In a further variant of the invention the diameter of the first anchoring element is equal to the diameter of the second anchoring element or the diameter of the first anchoring element is greater than the diameter of the second anchoring element, since the diameter of the atrial appendage often reduces over the distance from the atrial appendage entrance.

According to a particularly preferred variant of the invention the first anchoring element and/or the second anchoring element has a first sub-portion and a second sub-portion, wherein the first sub-portion extends radially outwardly and the second sub-portion is folded back radially inwards, particularly in such a way that the first sub-portion and the second sub-portion are folded to a double-layer. A double-layered anchoring element has a better stability and therefore an enhanced anchoring at the atrial appendage tissue wall. During the implantation first the second sub-portion unfolds and during radially outwardly folding the first sub-portion the second sub-portion folds back onto the first sub-portion. This sequentially folding of the first sub-portion and the second sub-portion has the advantage that during the implantation a minimal space is required. Further the first unfolding of the second sub-portion and the following folding back onto the first sub-portion has the advantage that the second sub-portion can engage into the muscles located inside the atrial appendage, whereby the device is securely fixed in the atrial appendage.

According to a further inventive variant the first anchoring element and/or the second anchoring element is coiled, particularly like a spiral. This also enhances the stability of the anchoring element and therefore the anchoring at the atrial appendage tissue wall.

In a preferred variant of the invention the backfolding or coiling of the first anchoring element and/or the second anchoring element is located towards the closing element. Thus, particularly a relocation of the inventive device in the direction of the atrial appendage entrance is avoided.

According to a further preferred variant of the invention the outer rim of the first anchoring element and/or the second anchoring element is built by loops or slings. The loops or slings are located next to each other or partially overlap each other, such that the outer rim of the first anchoring element and/or the second anchoring element is wavelike. A wavelike outer rim of the first anchoring element and/or the second anchoring element enhances the anchoring of the inventive device at the atrial appendage tissue wall.

Advantageously the outer rim of the first anchoring element and/or the second anchoring element is built by loops or slings with the same size. This results to a regular wave-form outer rim of the first anchoring element and/or second anchoring element.

Alternatively the outer rim of the first anchoring element and/or the second anchoring element is built by loops or slings of different sizes, for example one big loop or sling after two or three small loops or slings. Particularly a combination of the folding back of a sub-portion of the first anchoring element and/or the second anchoring element relative to another sub-portion of the first anchoring element and/or second anchoring element with groups or slings of different sizes results in an enhanced anchoring of the inventive device at the atrial appendage tissue wall because the bigger loops or slings can engage muscles inside the atrial appendage during the backfolding.

According to a preferred variant of the invention the device can be relocated and/or explanted, for example using a coupling element for an implantation instrument.

In a further preferred inventive variant the device has in a first operating state (primary form) a large ratio of length to lateral extension along the longitudinal axis of the device and in a second operating state (secondary form) a smaller ratio of length to lateral extension along the longitudinal axis of the device and the device can be reversibly deformed against elastic material forces from the secondary form to the primary form. The inventive device is thereby easily implantable using a minimal invasive method into the atrial appendage of a patient.

BRIEF DESCRIPTION OF THE DRAWINGS

In the following the invention is explained with respect to embodiments shown in the figures. It shows.

DETAILED DESCRIPTION

Figure 1:
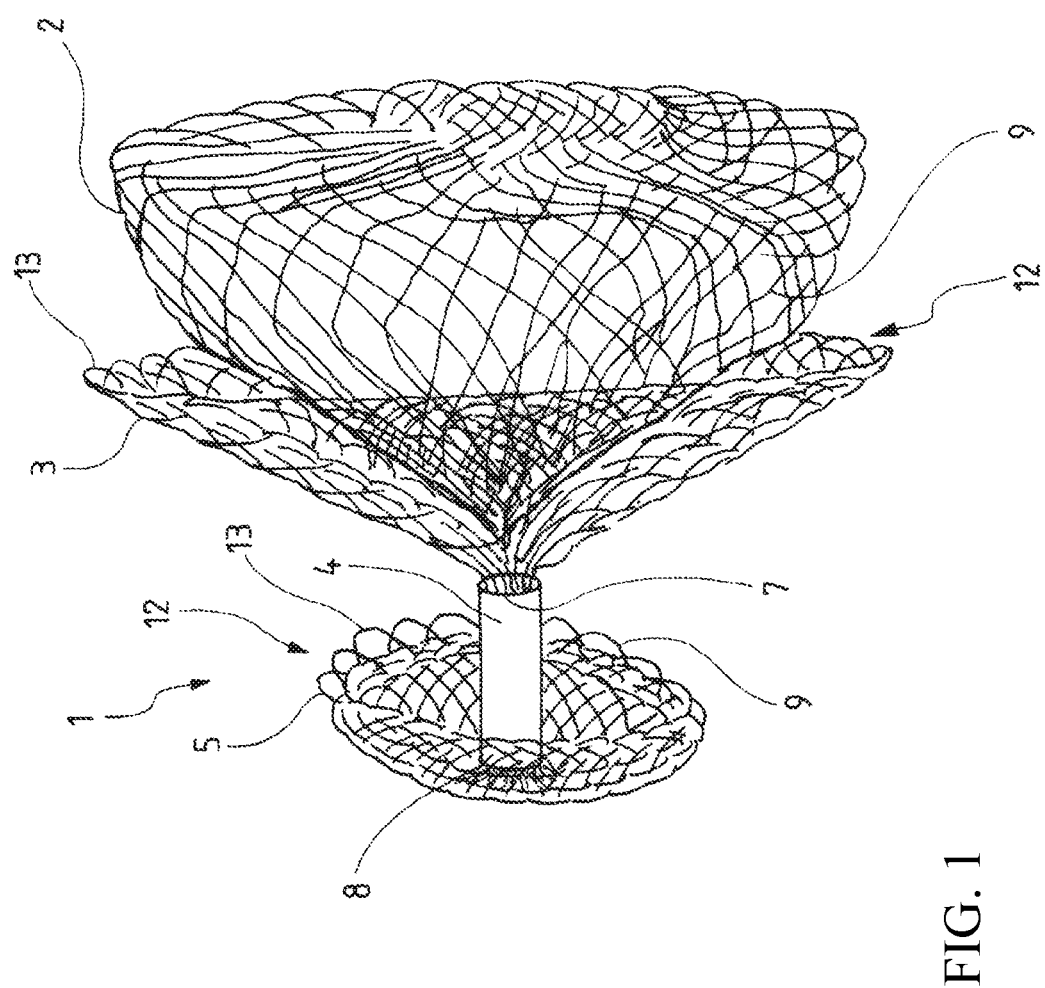
FIG. 1: a perspective view of an inventive device.

FIG. 1 shows a perspective view of an inventive device 1 for closing an atrial appendage, particularly the left atrial appendage. The device 1 comprises a closing element 2 (which may be referred to as a closer), designed to be arranged in an atrial appendage entrance and to prevent an entrance of blood into the atrial appendage and/or a leakage of thrombus out of the atrial appendage. The closing element 2 is configured that it does not, in the implanted state, protrude out of the atrial appendage into the atrium of the heart.

The device 1 further comprises a first anchoring element 3 (which may be referred to as a first anchor), which is arranged adjacent to the closing element 2 and connected to the closing element 2, wherein the first anchoring element 3 is designed for an anchoring on an atrial appendage tissue wall.

The device 1 furthermore comprises a connecting element 4 (which may be referred to as a connector), which is at least in a radial direction flexible and connected to the first anchoring element 3.

Further the device 1 comprises a second anchoring element 5 (which may be referred to as a second anchor), which is connected to the connecting element 4 and designed for an anchoring on an atrial appendage tissue wall.

The diameter of the closing element 2 is larger than the atrial appendage entrance.

The diameter of the closing element 2 is between 5% and 20% larger than the atrial appendage entrance, particularly about 10%.

The closing element 2 has a truncated cone-shape in the area of the atrial appendage entrance and further in the direction of the inner atrial appendage a conical area. The surface of the closing element 2 directed towards the atrium of the heart is smooth.

After the conical area of the closing element 2 the first anchoring element 3 is located. In the embodiment according to FIG. 1 the closing element 2 and the first anchoring element 3 are built integrally.

The connecting element 4 is connected to the first anchoring element 3 via a first connection 7 and connected to the second anchoring element 5 via a second connection 8. The first connection 7 and the second connection 8 are located at opposing ends of the connecting element 4.

According to FIG. 1 the connecting element 4 is cylindrical and helical.

The closing element 2 and the first anchoring element 3 are built integrally from a single wire-type element 9 by intercoiling and/or interwining and/or interweaving like a tissue and/or a cluster and/or a net. The second anchoring element 5 is also formed from a single wire-type element 9 by intercoiling and/or interwining and/or interweaving like a tissue and/or a cluster and/or a net. The wire-type elements 9 building the closing element 2 and the first anchoring element 3 respectively the second anchoring element 5 consists of a shape memory material. In the embodiment according to FIG. 1 the wire-type element 9 consists of nitinol.

The device 1 of FIG. 1 can further comprise a radio-opaque marking, particularly a marker, marking tag of marking wire. Using the radio-opaque marking, the positioning of the device 1 can be monitored during the implantation using an imaging method like e. g. x-ray or magnetic resonance imaging.

As can also be seen in FIG. 1 the first anchoring element 3 and the second anchoring element 5 extend in a radial direction. The first anchoring element 3 and the second anchoring element 5 are umbrella-shaped, wherein the opening of the umbrella is directed towards the atrial appendage entrance respectively the closing element 2. Alternatively the first anchoring element 3 and/or the second anchoring element 5 can be bulbous and/or curved. The cavity created by the bulbous and/or curved design is directed towards the atrial appendage entrance respectively the closing element 2.

The diameter of the first anchoring element 3 is larger than the diameter of the second anchoring element 5 since usually the atrial appendage narrows over the distance from the atrial appendage entrance and the first anchoring element 3 is located nearer to the atrial appendage entrance than the second anchoring element 5.

The outer rim 12 of the first anchoring element 3 and of the second anchoring element 5 is built by loops or slings 13. In the embodiment according to FIG. 1 the outer rim 12 of the first anchoring element 3 and of the second anchoring element 5 is built by loops or slings 13 with the same size which results in a wave-like outer rim 12.

The device 1 for closing an atrial appendage, particularly the left atrial appendage, of FIG. 1 has in a first operating state (primary form) a large ratio of length to lateral extension along the longitudinal access of the device 1 and in a second operating state (secondary form) a smaller ratio of length to lateral extension along the longitudinal access of the device 1. The device 1 can be reversibly deformed against elastic material forces from the secondary form to the primary form. By applying a force against the elastic material forces the device 1 of FIG. 1 is reversibly transformed to the primary form. In the primary form the inventive device 1 can be implanted in an atrial appendage of a patient using a minimal invasive method through a catheter. Therefore the device 1 is expanded in the longitudinal direction of the device 1, so that the device 1 has an essentially cylindrical form. In this cylindrical form the device 1 can be pushed via a catheter into the atrial appendage. As soon as the device 1 exits the distal end of the catheter the device 1 transfers back to the secondary form. At first the second anchoring element 5 exits the distal end of the catheter, whereby the second anchoring element 5 is anchored on the atrial appendage tissue wall. During the further implantation of the inventive device 1 the connecting element 4 exits the distal end of the catheter. Afterwards the first anchoring element 3 exits the distal end of the catheter and is anchored to the atrial appendage tissue wall. At last the closing element 3 exits the distal end of the catheter and is located inside the atrial appendage entrance to prevent an entrance of blood into the atrial appendage and/or a leakage of thrombus out of the atrial appendage. In the implanted state the closing element 2 does not protrude out of the atrial appendage into the atrium of the heart. The exact positioning of the inventive device 1 can be monitored using an imaging method like x-ray or magnetic resonance imaging. Depending on the material of the inventive device 1 the inventive device 1 can also comprise a radio-opaque marking.

After the positioning of the inventive device 1 has been checked using an imaging method the connection between the inventive device 1 and the instruments used during implantation is separated, so that the inventive device 1 can remain in the atrial appendage and can be overgrown by endothelial tissue, particularly in the area of the atrial appendage entrance, as fast as possible within the next weeks or months.

Figure 2:
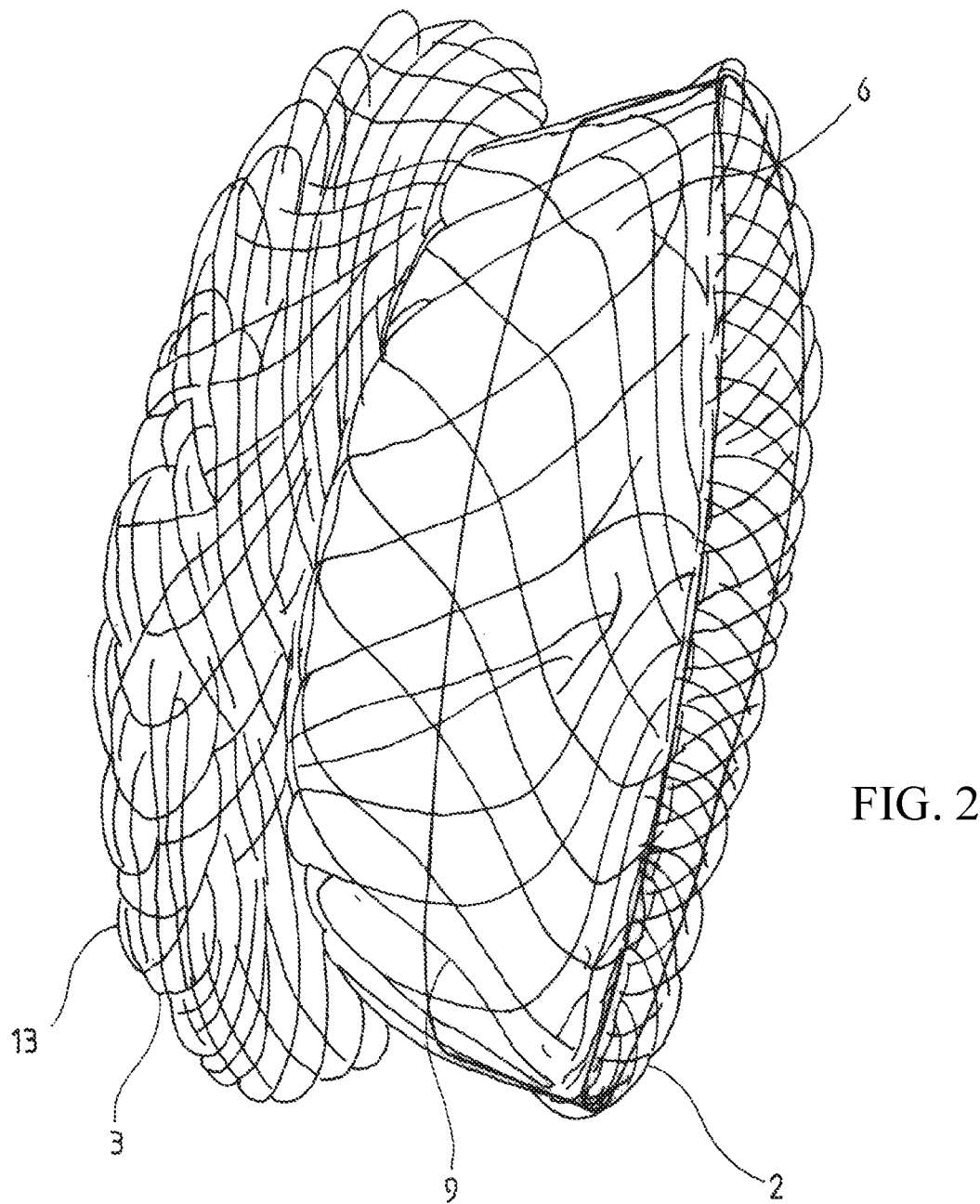
FIG. 2: a detailed view of a closing element.

FIG. 2 shows a detailed view of the closing element 2 of an inventive device 1. The closing element 2 is designed to be arranged in an atrial appendage entrance and to prevent an entrance of blood into the atrial appendage and/or a leakage of thrombus out of the atrial appendage. The closing element 2 is configured that it does not, in the implanted state, protrude out of the atrial appendage into the atrium of the heart.

As also shown in FIG. 1 the closing element 2 is integrally built with the first anchoring element 3, which is arranged adjacent to the closing element 2. The first anchoring element 3 is designed for an anchoring for an atrial appendage tissue wall.

The closing element 2 can comprise a first membrane element 6, wherein the first membrane element 6 is impermeable to thrombus and for example porous. Alternatively or additionally the closing element 2 can comprise a second membrane element 6, wherein the second membrane element 6 is designed to support an overgrow of the closing element 2 with endothelial tissue. The first membrane element 6 and the second membrane element 6 can be built integrally as shown in FIG. 2. The membrane element 6 comprises at least one of the following materials: polyester, polytetrafluorethylene (PTFE), expanded/extruded PTFE, teflon, felt, goretex, siliconeurethane, metal fibers and polypropylene.

The membrane element 6 is designed in such a way that it completely covers the atrial appendage entrance in the implanted state of the device 1. Therefore the membrane element 6 completely covers the surface of the closing element 2 directed to the atrium of the heart. Furthermore the membrane element 6 encloses the rim of the closing element 2 in such a way, that the membrane element 6 completely contacts the atrial appendage tissue wall at the entrance in the implanted state of the device 1. Therefore the membrane element 6 is in the area of the truncated cone-shaped closing element 2 located at the conical side-face of the truncated cone-shaped closing element 2. The membrane element 6 can be located outside of the closing element 2 as well as inside the closing element 2, directly adjacent to the walls of the closing element 2. In the embodiment shown in FIG. 2 the membrane element 6 is located inside the closing element 2, directly adjacent to the wire-type element 9 from which the closing element 2 is built. Since the closing element 2 has a netstructure the membrane element 6 is in direct contact with the atrial appendage, which supports an overgrow with endothelial tissue.

Figure 3:
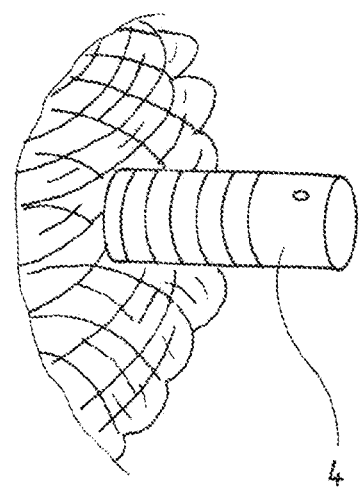
FIG. 3: a detailed view of a connecting element.

FIG. 3 shows a detailed view of a connecting element 4 of an inventive device 1 for closing an atrial appendage, particularly the left atrial appendage. The connecting element 4 is in a radial direction flexible and connected at a first end to the first anchoring element 3 and at a second end, opposing the first end, connected with the second anchoring element 5. The connecting element 4 is in a radial direction flexible so that the inventive device 1 can adapt to the anatomy of the atrial appendage.

The connecting element 4 of FIG. 3 is built of a tube by cutting apertures into the tube for example using a laser. By cutting apertures into the tube the connecting element 4 is at least over a part of its length helical.

The connection between the connecting element 4 and the first anchoring element 3 or the second anchoring element 5 is particularly detachable. Such a detachable connection is for example built by apertures in the wall of the connecting element 4 through which locking wires are guided which extend through the inner cavity of the connecting element 4 and through the walls of the first anchoring element 3 or the second anchoring element 5. Therefore for example in the area of the first anchoring element 3 or the second anchoring element 5 inside the cavity of the connecting element 4 apertures are located. Through these apertures locking wire is guided, which also passes through the first anchoring element 3 or the second anchoring element 5. Before an implantation of the inventive device 1 the locking wires are welded or knotted so that the connection is non-detachable in the implanted state of the device 1.

Figure 4:
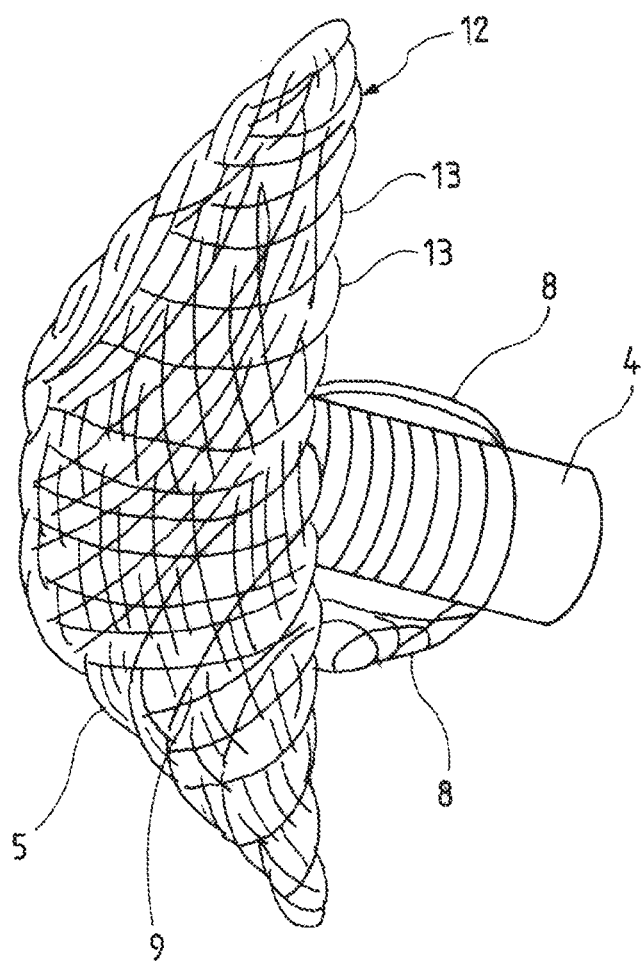
FIG. 4: a detailed view of a second anchoring element.

FIG. 4 shows a detailed view of the second anchoring element 5. The second anchoring element 5 is for example built by a single wire-type element 9. In the shown embodiment of FIG. 4 the second anchoring element 5 is double-layered, wherein each layer consists of a single wire-type element 9. Both layers of the second anchoring element 5 are interlaced at the rim 12. The outer rim 12 of the second anchoring element 5 is built by loops or slings 13 which results in a wave-like outer rim 12. Such a wave-like outer rim 12 is particularly suitable for an anchoring on the atrial appendage tissue wall without perforating the atrial appendage tissue wall since such a wave-like outer rim 12 has no sharp edges. The second anchoring element 5 is umbrella-shaped, wherein the cavity of the umbrella is directed towards the atrial appendage entrance. With respect to a device 1 for closing an atrial appendage normally there only is a risk that the device 1 relocated towards the atrium of the heart. Such a relocation is prevented using an umbrella-shaped anchoring element 3, 5 where the cavity of the umbrella-shaped element is directed towards the atrial appendage entrance. According to FIG. 4 the second connection 8 between second anchoring element 5 and the connecting element 4 is realized by guiding the wire-type elements 9 of the second anchoring element 5 through apertures in the circumference wall of the connecting element 4.

Figure 5:
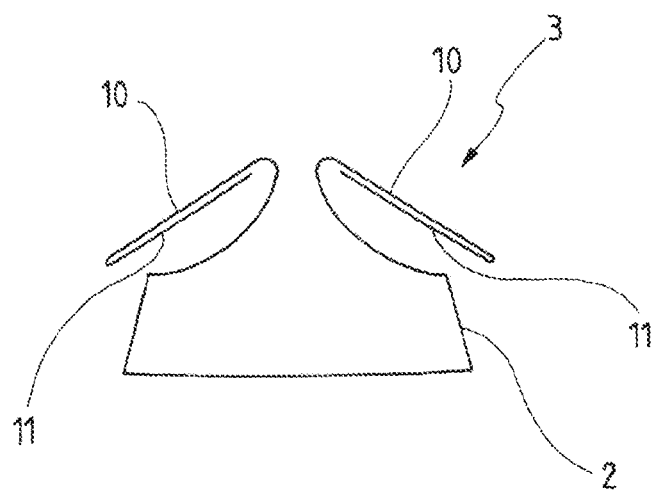
FIG. 5: a schematic view of a further closing element.

FIG. 5 shows a schematic view of a further closing element 2 with a first anchoring element 3. The first anchoring element 3 shown in FIG. 5 differs from the first anchoring element 3 of FIG. 1 and FIG. 2 in that the first anchoring element 3 comprises a first sub-portion 10 and a second sub-portion 11, wherein the first sub-portion 10 extends radially outwardly and the second sub-portion 11 is folded back radially inwards. As can be seen from FIG. 5 the first sub-portion 10 and the second sub-portion 11 are backfolded to a double-layer, whereby the stability of the first anchoring element 3 is enhanced which leads to a better anchoring of the first anchoring element 3 on the atrial appendage tissue wall.

Figure 6:
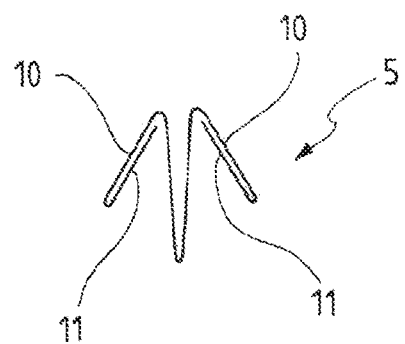
FIG. 6: a schematic view of a second anchoring element.

FIG. 6 shows a schematic view of a further second anchoring element 5 of a device 1 for closing an atrial appendage, particularly a left atrial appendage. The second anchoring element 5 of FIG. 6 differs from the second anchoring element 5 of FIG. 1 and FIG. 4 in that the second anchoring element 5 as a first sub-portion 10 and a second sub-portion 11, wherein the first sub-portion 10 extends radially outwardly and the second sub-portion 11 is folded back radially inwards, particularly in such a way that the first sub-portion 10 and the second sub-portion 11 are folded to a double-layer. The second anchoring element 5 of FIG. 6 is umbrella-shaped, wherein the cavity of the umbrella is directed towards the atrial appendage entrance.

The backfolding of the second sub-portion 11 to the first sub-portion 10 as shown in FIG. 5 and FIG. 6 is directed towards the closing element 2.

Figure 7:
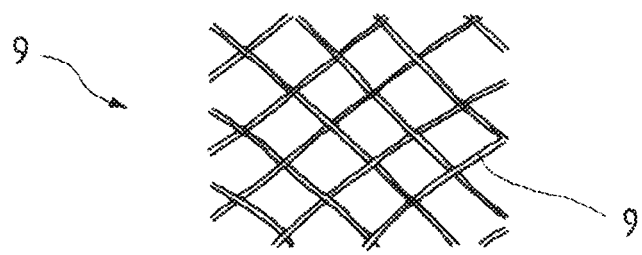
FIG. 7: a schematic view of a structure of a closing element and/or an anchoring element.

FIG. 7 shows a schematic view of a structure of a closing element 2 and/or anchoring element 3, 5. In case the closing element 2, the first anchoring element 3 and/or the second anchoring element 5 is built of a single wire-type element 9 or multiple wire-type elements by intercoiling and/or interwining and/or interweaving like a tissue and/or a cluster and/or a net a structure as shown in FIG. 7 is achieved. In FIG. 7 the tissue and/or cluster and/or net is formed of a single wire-type element 9.

Figure 8:
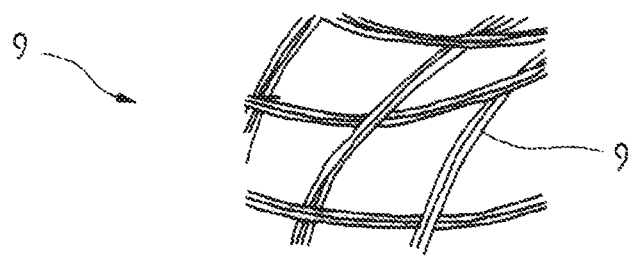
FIG. 8: a schematic view of a further structure of a closing element and/or anchoring element.

FIG. 8 shows a schematic view of a further structure of a closing element 2 and/or anchoring element 3, 5, wherein the structure is built by a single wire-type element 9 and wherein the single wire-type element 9 consists of multiple wires which extend parallel to each other.

Figure 9A:
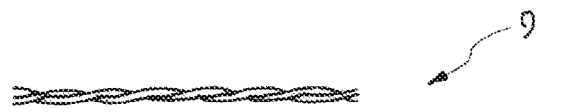
FIG. 9a: a schematic view of an embodiment of a wire-type element.
Figure 9B:
FIG. 9b: a schematic view of another embodiment of a wire-type element.
Figure 9C:
FIG. 9c: a schematic view of another embodiment of a wire-type element.

FIGS. 9a to 9c show further schematic views of embodiments of wire-type elements 9, wherein the wire-type elements 9 consists of several wires which are interlaced or twisted with each other which results in a so-called litz-wire.

Figure 10:
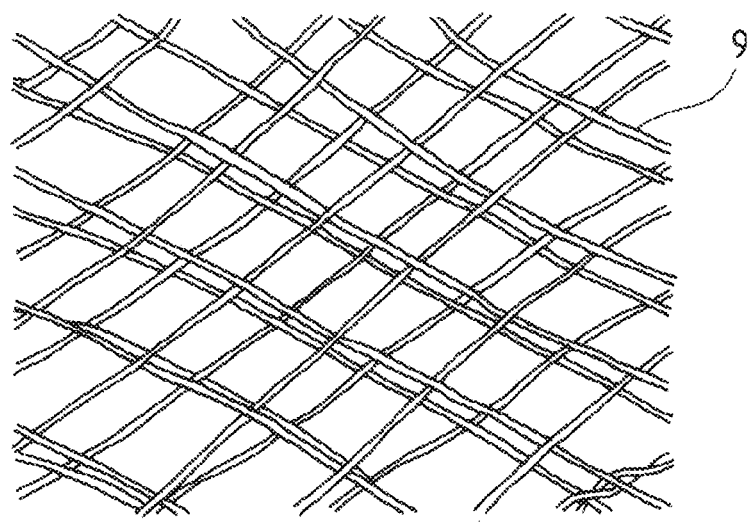
FIG. 10: a schematic view of a double-layered closing element and/or anchoring element.
Figure 11:
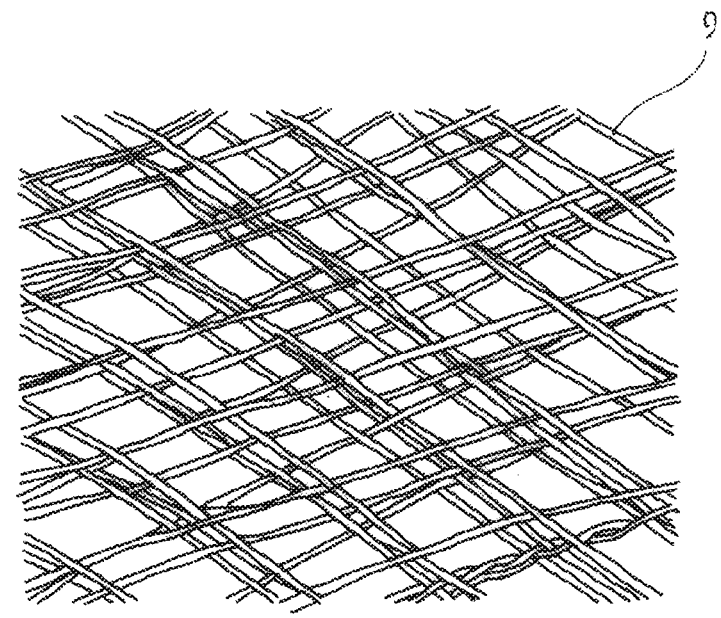
FIG. 11: a schematic view of a multiple layered closing element and/or anchoring element.

As can be seen in FIG. 10 and FIG. 11 the closing element 2 and/or the anchoring element 3, 5 are double-layered (FIG. 10) or multi-layered (FIG. 11). This enhances the stability of device 1. Furthermore for example between the single layers one or more membrane elements 6 can be located.

Figure 12:
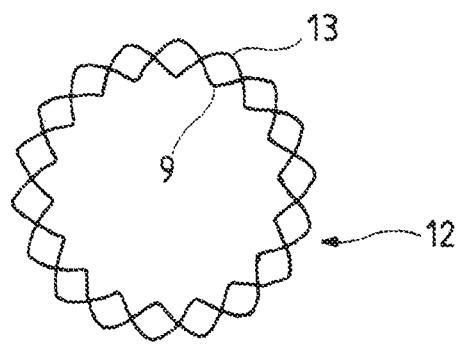
FIG. 12: a schematic view of a first embodiment of an outer rim of an anchoring element.

FIG. 12 shows a schematic view of a first embodiment of an outer rim 12 of anchoring element 3, 5. The outer rim 12 is built by loops or slings 13 of the same size, which results in a wave-like outer rim. Such a wave-like outer rim 12 improves the anchoring of the anchoring element 3, 5 on the atrial appendage tissue wall.

Figure 13:
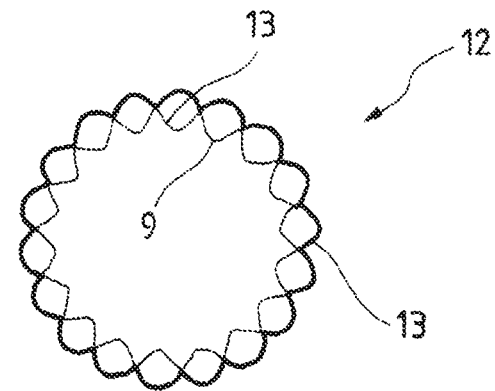
FIG. 13: a schematic view of a second embodiment of an outer rim of an anchoring element.

FIG. 13 shows a schematic view of a second embodiment of an outer rim 12 of an anchoring element 3, 5. The outer rim 12 according to FIG. 13 differs from the outer rim 12 according to FIG. 12 in that the outer rim 12 is reinforced. The reinforcement can be for example directly integrated into the wire-type element 9 or can be achieved by overlaying multiple wire-type elements 9 in the area of the loops or slings 13.

Figure 14:
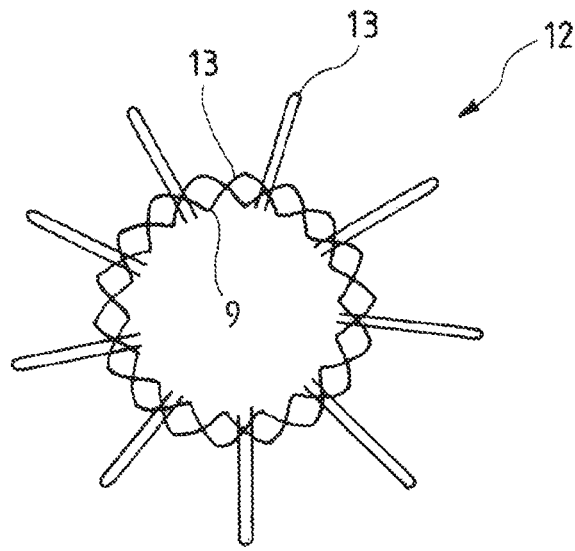
FIG. 14: a schematic view of a third embodiment of an outer rim of an anchoring element.

FIG. 14 shows a schematic view of a third embodiment of an outer rim 12 of anchoring elements 3, 5. The outer rim 12 of the anchoring elements 3, 5 is built by loops or slings 13 of different sizes. The distribution of the loops or slings 13 with different sizes is regularly. According to FIG. 14 one big loop or sling 13 is located after two small loops or slings 13. Such an embodiment using different sizes of loops or slings 13 is particularly advantageous in combination which a backfolding of a sub-portion 11 onto another sub-portion 10, wherein the backfolded sub-portion 11 is built by larger loops or slings 13. During the backfolding of the large loops or slings 13 these can engage into muscles located inside of the atrial appendage, whereby the anchoring of the inventive device 1 inside the atrial appendage is improved.

As shown in FIG. 13 the outer rim 12 according to FIG. 14 can also be reinforced.

LIST OF REFERENCED ELEMENTS 1 device
2 closing element
3 first anchoring element
4 connecting element
5 second anchoring element
6 membrane element
7 first connection
8 second connection
9 wire-type element
10 first sub-portion
11 second sub-portion
12 outer rim
13 loops and/or slings

What is claimed is:

1. A device to close an atrial appendage, comprising:
a closer configured to be arranged in an atrial appendage entrance of the atrial appendage, and configured to prevent at least one of an entrance of blood into the atrial appendage and a leakage of thrombus out of the atrial appendage, and configured such that the closer does not, in an implanted state, protrude out of the atrial appendage into an atrium of a heart and a terminal end surface of the closer directed towards the atrium of the heart, in the implanted state, is smooth such that the closer will not extend into the atrium of the heart;
a first anchor arranged adjacent to the closer and connected to the closer, wherein the first anchor is configured to anchor directly to the atrial appendage in the implanted state;
a connector which is, at least in a radial direction, flexible and connected to the first anchor;
a second anchor connected to the connector, wherein the second anchor is configured to anchor directly to the atrial appendage in the implanted state;
wherein the first anchor and the second anchor each have an umbrella shape having a cavity;
wherein the cavity of each umbrella shape is directed towards the atrial appendage entrance; and
wherein the first anchor is arranged relative to the closer such that, in the implanted state a portion of the closer resides within the cavity of the umbrella shape of the first anchor.

2. The device according to claim 1, wherein a diameter of the closer is configured to be larger than the atrial appendage entrance.

3. The device according to claim 2, wherein the diameter of the closer is configured to be between 5% and 20% larger than the atrial appendage entrance.

4. The device according to claim 1, wherein the closer comprises a first membrane element, wherein the first membrane element is impermeable to thrombus.

5. The device according to claim 4, wherein the closer comprises a second membrane element, wherein the second membrane element is configured to support an overgrow of the closer with endothelial tissue.

6. The device according to claim 5, wherein the first membrane element and the second membrane element are integral.

7. The device according to claim 5, wherein at least one of the first membrane element and the second membrane element comprise at least one of the following materials: polyester, polytetrafluoroethylene, felt, silicone-urethane, metal fibers, and polypropylene.

8. The device according to claim 5, wherein at least one of the first membrane element and the second membrane element completely covers the atrial appendage entrance in the implanted state of the device.

9. The device according to claim 5, wherein at least one of the first membrane element and the second membrane element enclose a rim of the closer such that, in the implanted state of the device, at least one of the first membrane element and the second membrane element is configured to completely contact a tissue wall of the atrial appendage at the enclosed rim.

10. The device according to claim 1, wherein the closer is at least one of cylindrical, conical, tapered and truncated cone-shaped.

11. The device according to claim 1, wherein the closer and the first anchor are formed integrally, or formed separately and securely fixed to one another.

12. The device according to claim 1, wherein the connector is connected to the first anchor via a first connection.

13. The device according to claim 12, wherein the connector is connected to the second anchor via a second connection.

14. The device according to claim 13, wherein the first connection and the second connection are located on opposing ends of the connector.

15. The device according to claim 1, wherein the connector is cylindrical.

16. The device according to claim 1, wherein the connector is helical.

17. The device according to claim 1, wherein the connector is made of a tube.

18. The device according to claim 1, wherein at least one of the closer, the first anchor and the second anchor is formed from at least one of a single wire-type element and multiple wire-type elements by at least one of intercoiling, intertwining and interweaving.

19. The device according to claim 1, wherein at least one of the closer, the first anchor and the second anchor consist of a shape memory material.

20. The device according to claim 1, further comprising a radio-opaque marking.

21. The device according to claim 1, wherein a diameter of the first anchor is equal to a diameter of the second anchor, or the diameter of the first anchor is greater than the diameter of the second anchor.

22. The device according to claim 1, wherein at least one of the first anchor and the second anchor have a first sub-portion and a second sub-portion, wherein the first sub-portion extends radially outwardly and the second sub-portion is folded back radially inwards such that the first sub-portion and the second sub-portion are folded to a double-layer.

23. The device according to claim 22, wherein the back-folding of at least one of the first anchor and the second anchor is directed towards the closer.

24. The device according to claim 1, wherein an outer rim of at least one of the first anchor and the second anchor is formed by at least one of loops and slings.

25. The device according to claim 24, wherein the outer rim of at least one of the first anchor and the second anchor is formed by at least one of a plurality of loops each with a same size and a plurality of slings each with a same size.

26. The device according to claim 24, wherein the outer rim of at least one of the first anchor and the second anchor is formed by at least one of a plurality of loops each with different sizes and a plurality of slings each with different sizes.

27. The device according to claim 26, a distribution of the at least one of loops and slings with different sizes is repetitive.

28. The device according to claim 1, wherein the device has, in a first operating state as a primary form, a first ratio of length to lateral extension along a longitudinal axis of the device, and, in a second operating state as a secondary form, a second ratio of length to lateral extension along the longitudinal axis of the device, wherein the first ratio of length to lateral extension along the longitudinal axis is larger than the second ratio of length to lateral extension along the longitudinal axis of the device, and the device is reversibly deformable against elastic material forces from the secondary form to the primary form.

29. The device according to claim 1, wherein the device has a longitudinal axis with the closer, the first anchor and the second anchor arranged on the longitudinal axis, and wherein, on the longitudinal axis in the implanted state, the first anchor is closer to the closer than the first anchor is to the second anchor.

\* \* \* \* \*